United States Patent [19]

Belliotti et al.

[11] Patent Number: 5,017,604

[45] Date of Patent: May 21, 1991

[54] NOVEL FENAMIC ACID METHYL HYDROXAMATE DERIVATIVES HAVING CYCLOOXYGENASE AND 5-LIPOXYGENASE INHIBITION

[75] Inventors: Thomas R. Belliotti, Ypsilanti; Catherine R. Kostlan, Saline, both of Mich.

[73] Assignee: Warner-Lambert Company, Morris Plains, N.J.

[21] Appl. No.: 508,143

[22] Filed: Apr. 11, 1990

[51] Int. Cl.$^5$ .............................................. A61K 31/27
[52] U.S. Cl. ..................................... 514/482; 514/513; 514/535; 560/18; 560/27; 560/34; 560/37; 562/432; 562/439; 562/442; 562/451; 558/233
[58] Field of Search ...................... 560/18, 27, 34, 37, 560/42; 558/233; 562/432, 439, 442, 451; 514/482, 513, 535

[56] References Cited

U.S. PATENT DOCUMENTS

| | | | |
|---|---|---|---|
| 3,413,313 | 11/1968 | Scherrer | 260/340.9 |
| 4,029,815 | 6/1977 | Sherlock et al. | 424/309 |
| 4,981,865 | 1/1991 | Belliotti | 560/27 |

FOREIGN PATENT DOCUMENTS

| | | | |
|---|---|---|---|
| 0196184 | 10/1986 | European Pat. Off. | |
| 0196674 | 10/1986 | European Pat. Off. | |
| 1246749 | 8/1962 | Fed. Rep. of Germany | 560/37 |

OTHER PUBLICATIONS

English translation of JP 24578/67.
Justus Liebigs Annalen Der Chemie, Part 7/8, 1975, Verlag Chemie, p. 1245–1251.
J6724578 Ser. Abs. No. 11330d, N7008620 Der. Abs. No. 009745-B.

Primary Examiner—Bruce Gray
Attorney, Agent, or Firm—Joan Thierstein

[57] ABSTRACT

The present invention is novel selected hydroxamic acid derivatives of fenamic acids having 5-lipoxygenase and cyclooxygenase inhibiting properties, pharmaceutical compositions for treating conditions advantageously affected by the inhibition and methods for treating these conditions in mammals, including humans suffering therefor.

40 Claims, No Drawings

NOVEL FENAMIC ACID METHYL HYDROXAMATE DERIVATIVES HAVING CYCLOOXYGENASE AND 5-LIPOXYGENASE INHIBITION

BACKGROUND OF THE INVENTION

The present invention is novel derivatives of fenamic acids. Such fenamic acids are related to the fenamic acids in copending application U.S. Ser. No. 248,204 (or published WO 89/03818) so the "Background of the Invention" from this application is pending incorporated by reference.

Additionally, Japanese Application Nos. J63185-924A and J63189-923A (disclosed in Derwent Abstract Nos. 88-25448/36 and 88-25447/36, respectively) and Netherlands Application No. 7008620 (disclosed in Derwent Abstract 009745-B) include hydroxyamino. The present fenamic acid derivatives differ in that a hydroxamate substituent in the present invention is removed from the benzanilino ring system by only one —$CHR_2$—group, and the substituent on the phenyl not containing the hydroxamate substituent has only one group which is $CO_2R_1$. Other references of interest include U.S. Pat. No. 3,821,268 having a hydroxyamino removed from a benzanilino moiety by an acyl group and U.S. Pat. No. 3,574,737 having a hydroxyamino removed from a benzanilino moiety by an acyloxy group. U.S. Pat. No. 3,413,313 teaches an N-aryl-anthranilic acid having a carboxy on an N-phenyl group with a ketoxime of the formula —C(NOH)lower alkyl. The present invention differs in that N-phenyl group is substituted with a substituted hydroxylamine rather than a ketoxime, and is thus at a different oxidation state.

Thus, the present invention are to selected novel derivatives of fenamates and pharmaceutically acceptable acid addition or base salts thereof, pharmaceutical compositions for treating inflammation, arthritis, pain, pyrrhia, and the methods for such treatment.

SUMMARY OF INVENTION

The present invention is a novel compound of the formula I

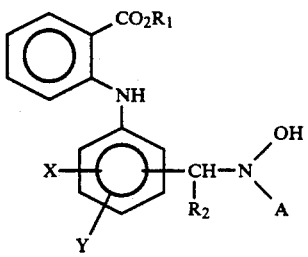

wherein
$R_1$ is hydrogen or lower alkyl;
$R_2$ is hydrogen or lower alkyl;
X is hydrogen, halogen, trifluoromethyl, lower alkyl, lower alkoxy, or hydroxy;
Y is hydrogen, halogen, trifluoromethyl, lower alkyl, lower alkoxy, or hydroxy;
A is hydrogen, lower alkyl,

wherein W is S or O and Z is hydrogen, lower alkyl, lower alkoxy, or $NR_3R_4$ wherein $R_3$ and $R_4$ are independently hydrogen or lower alkyl; and pharmaceutically acceptable acid addition or acid and base salts thereof.

The present invention is also a pharmaceutical composition for the treatment of conditions advantageously affected by the inhibition of 5-lipoxygenase and/or cyclooxygenase which comprises administering an amount effective for inhibiting 5-lipoxygenase and/or cyclooxygenase of a novel compound of the formula I as defined above; and pharmaceutically acceptable acid addition or base salts thereof and a pharmaceutically acceptable carrier.

Further, the present invention also provides a method of use for a compound of the formula I or physiologically acceptable acid addition or base salt thereof as defined above for use as an inhibitor of the lipoxygenase and/or cyclooxygenase enzymes of the mammalian, including human, arachidonic acid metabolism, which method comprises inhibition of such enzymes by administration to a mammal of a lipoxygenase and/or cyclooxygenase inhibiting amount of any such compound or salt in unit dosage form, and to use of any such compound or salt in the manufacture of lipoxygenase and/or cyclooxygenase inhibitor agents.

Further, the present invention also provides any compound or composition of formula (1) (as hereinbefore defined) or physiologically acceptable salt thereof, for use as a medical therapeutic and/or prophylactic agent, to methods of medical therapeutic and/or prophylactic treatment by administration to a mammal of a medically therapeutic and/or prophylactic effective amount of any such compound or salt, and to use of any such compound or salt in the manufacture of medical therapeutic and/or prophylactic agents. The kinds of medical therapy and prophylaxis pertinent to the foregoing and therefore in that sense comprising part of the present invention, are elaborated by way of example in the following paragraphs which are not intended to be construed as in any way limiting the scope of these aspects of said invention.

Disease or conditions benefiting from lipoxygenase and/or cyclooxygenase inhibition according to the present invention are rheumatoid arthritis, osteoarthritis, other inflammatory conditions, psoriasis, allergic diseases, asthma, inflammatory bowl disease, GI ulcers, cardiovascular conditions including ischemic heart disease, atherosclerosis, and ischemia-induced cell damage particularly brain damage caused by stroke. Preferred use of the present inventions is as an antiinflammatory agent.

The most preferred compound of the present invention is 2-[[2-chloro-3-[[(ethoxycarbonyl)hydroxyamino]methyl]phenyl]amino]benzoic acid, methyl ester, which is shown in Example 40 hereinafter.

DETAILED DESCRIPTION OF THE INVENTION

In the compounds of formula (I) the term "lower alkyl" is meant to include a straight or branched alkyl group having one to six carbon atoms, such as, for example, methyl, ethyl, propyl, butyl, pentyl or hexyl, and isomers thereof.

Lower alkoxy is O-alkyl of from one to six carbon atoms as defined above for "lower alkyl".

Halogen is fluoro, iodo, chloro, or bromo. Appropriate compounds of formula I are useful in the free base form, the free acid form or in the form of base salts thereof, and in the form of acid addition salts. The four forms are within the scope of the invention. The compounds of this invention may also exist in hydrated or solvated forms. In practice, use of the salt form or hydrated or solvated forms amounts to use of the base form.

A tautomeric form of selected compounds of formula I would be recognized by an ordinarily skilled artisan to be within the present invention.

Pharmaceutically acceptable salts within the scope of the invention may be those derived from mineral acids such as hydrochloric acid and sulfuric acid; and organic acids such as ethanesulfonic acid, benzenesulfonic acid, p-toluenesulfonic acid, and the like, giving the hydrochloride, sulfate, ethanesulfonate, benzenesulfonate, p-toluenesulfonate, and the like, respectively or those derived from bases such as suitable organic and inorganic bases. Examples of pharmaceutically acceptable base addition salts with compounds of the present invention include organic bases which are nontoxic and strong enough to form such salts. These organic bases form a class whose limits are readily understood by those skilled in the art. Merely for purposes of illustration, the class may be said to include mono-, di-, and trialkylamines, such as methylamine, dimethylamine, and triethylamine; mono-, di-, or trihydroxyalkylamines such as mono-, di-, and triethanolamine; amino acids such as arginine, and lysine; guanidine; N-methylglucosamine; N-methylglucamine; L-glutamine; N-methylpiperazine; morpholine; ethylenediamine; N-benzylphenethylamine; tris(hydroxymethyl)aminomethane; and the like. (See for example, "Pharmaceutical Salts," *J. Pharm. Sci.*, 66(1):1-19 (1977).) Salts of inorganic bases include sodium, potassium, calcium or the like.

The acid addition salts of said basic compounds are prepared either by dissolving the free base or acid of compound I in aqueous or aqueous alcohol solution or other suitable solvents containing the appropriate acid or base and isolating the salt by evaporating the solution, or by reacting the free base of compound I with an acid as well as reacting compound I having an acid group thereon with a base such that the reactions are in an organic solvent, in which case the salt separates directly or can be obtained by concentration of the solution.

The compounds of the invention may contain an asymmetric carbon atom. Thus, the invention includes the individual stereoisomers, and mixtures thereof. The individual isomers may be prepared or isolated by methods known in the art.

The amount required of a compound of formula I or physiologically acceptable salt thereof to achieve a therapeutic effect will, of course, vary both with the particular compound, the route of administration and the mammal under treatment and the particular disorder or disease concerned. A suitable dose of a compound of formula I or physiologically acceptable salt thereof for a mammal suffering from, or likely to suffer from any condition as described hereinbefore is 0.1 µg-500 mg of base per kilogram body weight. In the case of systemic administration, the dose may be in the range 0.5 to 500 mg of base per kilogram body weight, the most preferred dosage being 0.5 to 50 mg/kg of mammal body weight for Example 5 to 25 mg/kg; administered two or three times daily. In the case of topical administration, e.g. to the skin or eye, a suitable dose may be in the range 0.1 ng-100 µg of base per kilogram, typically about 0.1 µg/kg.

In the case of oral dosing for the treatment or prophylaxis of airway smooth muscle constriction, or asthma, or bronchitis in general, due to any course, a suitable dose of a compound of formula (I) or physiologically acceptable salt thereof, may be as specified in the preceding paragraph, but most preferably is from 1 mg to 10 mg of base per kilogram, the most preferred dosage being from 1 mg to 5 mg/kg of mammal body weight, for example from 1 to 2 mg/kg. In the case of pulmonary administration for the latter indications, the dose may be in the range of from 2 µg to 100 mg, for example from 20 µg to 0.5 mg, especially 0.1 to 0.7 mg/kg.

It is understood that the ordinarily skilled physician or veterinarian will readily determine and prescribe the effective amount of the compound to prevent or arrest the progress of the condition for which treatment is administered. In so proceeding, the physician or veterinarian could employ relatively low doses at first, subsequently increasing the dose until a maximum response is obtained.

The usefulness of the compounds of the present invention as inhibitors of the 5-lipoxygenase enzyme, cyclooxygenase, or in treating related diseases or conditions may be demonstrated by their effectiveness in various standard test procedures. A description of each procedure follows.

ARBL/ARBC Whole Cell 5-Lipoxygenase and Cyclooxyqenase Assays

Materials

The rat basophilic leukemia cell line (RBL-1) was obtained from the American Type Culture Collection (Rockville, Md.).

Radioimmunoassay (RIA) kits for $LTB_4$ and $PGF_{2\alpha}$ determination were obtained from Amersham (Arlington Heights, Ill.) and Seragen (Boston, Mass.), respectively.

All tissue culture media were obtained from GIBCO (Grand Island, NY).

Method

RBL-1 cells are grown in suspension culture in Eagle's minimum essential medium supplemented with 12% fetal bovine serum at 37° C. in an incubator supplied with air-5% carbon dioxide. Cells are harvested by centrifugation. They are washed with cold phosphate buffered saline pH 7.4 (PBS; NaCl, 7.1 g; $Na_2HPO_4$, 1.15 g; $KH_2PO_4$, 0.2 g; and KCl, 0.2 g/L). Cells are finally suspended in PBS containing 1.0 mM calcium at a density of $2 \times 10^6$ cells/mL. Cells are incubated with and without test agent (in DMSO) (1% DMSO is without effect on arachidonic acid metabolism) for 10 minutes at room temperature. Calcium inonophore A23187 (5 µM) is added and cells are incubated for 7 minutes at 37° C. The reaction is stopped by chilling the tubes on ice for 10 minutes. Cells are separated by centrifugation and the supernatant is stored at −20°. Aliquots (100 µL) are analyzed for $LTB_4$ and $PGF_{2\alpha}$ using radioimmunoassay kits as provided by the supplier.

Table 1 contains biochemical data obtained from this whole cell assay as $IC_{50}$s which are calculated as the concentration of test compound causing 50% inhibition of $LTB_4$ or $PGF_{2\alpha}$ formation or in percent inhibition at the given micromolar concentration. N at 10 or 16 is not active at 10 μmolar or 16 μmolar.

ing subcutaneous, intramuscular, and intravenous), intraarticular, topical, nasal, or buccal administration.

TABLE 1

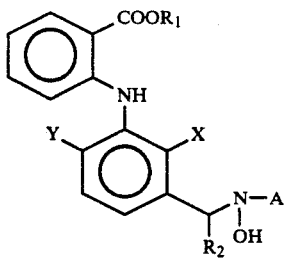

| Example | $R_1$ | Y | X | $R_2$ | A | ARBL IC50(μM) or % @ μM | ARBC IC50(μM) or % @ μM |
|---|---|---|---|---|---|---|---|
| 36 | Me | Me | Me | Me | C(O)Me | 100% @ 16[b] | N @ 16[d] |
| 43 | Me | Me | Me | Me | C(O)OEt | 100% @ 16[b] | N @ 16[d] |
| 52 | H | Me | Me | Me | C(O)Me | N @ 16[d] | N @ 16[d] |
| 53 | H | Me | Me | Me | C(O)OEt | N @ 16[d] | 53% @ 16[b] |
| 37 | Me | H | Cl | H | C(O)Me | 0.58[a] | 4.3[a] |
| 33 | Me | H | Cl | Me | C(O)Me | 100% @ 10[b] | N @ 10[c] |
| 40 | Me | H | Cl | H | C(O)OEt | 0.21[a] | 0.67[a] |
| 34 | Me | H | Me | H | C(O)Me | <0.0625[a] | 10[a] |
| 35 | Me | H | Me | Me | C(O)Me | 100% @ 10[b] | N @ 10[c] |
| 46 | Me | H | Cl | H | C(O)NHMe | 0.36[a] | 4.7[a] |
| 47 | H | H | Cl | H | C(O)Me | N @ 10[c] | 79% @ 10[b] |
| 54 | H | H | Cl | Me | C(O)Me | N @ 10[c] | 87% @ 10[b] |
| 41 | Me | H | Me | H | C(O)OEt | 0.39[a] | 8.7[a] |
| 44 | Me | H | Me | H | C(O)NHMe | >95% @ 16 | 43% @ 16[b] |
| 48 | H | H | Me | H | C(O)Me | N @ 10[c] | 1.9[a] |
| 51 | H | H | Me | Me | C(O)Me | N @ 16[d] | 70% @ 10[b] |
| 49 | H | H | Me | H | C(O)OEt | N @ 16[d] | 67% @ 0.25[b] |
| 50 | H | H | Me | H | C(O)NHMe | N @ 16[d] | 56% @ 16[b] |
| 38 | Me | Cl | Cl | H | C(O)Me | 0.36[a] | 6.0[a] |
| 42 | Me | Cl | Cl | H | C(O)OEt | 0.33[a] | 3.7[a] |
| 55 | H | Cl | Cl | H | C(O)Me | N @ 10[c] | 83% @ 10[b] |
| 56 | H | Cl | Cl | H | C(O)OEt | 47% @ 16[b] | 89% @ 16[b] |
| 39 | Me | Cl | Cl | Me | C(O)Me | 100% @ 10[b] | 52% @ 10[b] |
| 57 | H | Cl | Cl | Me | C(O)Me | N @ 10[c] | 53% @ 10[b] |

[a]IC50 in Micromolar
[b]% inhibition at the given micromolar concentration
[c]N @ 10 μmolar is not active at 10 μmolar.
[d]N @ 16 μmolar is not active at 16 μmolar.

While it is possible for an active ingredient to be administered alone, it is preferable to present it as a pharmaceutical formulation comprising a compound of formula I or a pharmacologically acceptable acid addition salt thereof and a physiologically acceptable carrier therefor. Such formulations constitute a further feature of the present invention. Conveniently, the active ingredient comprises from 0.1% to 99.9% by weight of the formulation. Conveniently, unit doses of a formulation contain between 0.1 mg and 1 g of the active ingredient. For topical administration, the active ingredient preferably comprises from 1% to 2% by weight of the formulation but the active ingredient may comprise as much as 10% w/w. Formulations suitable for nasal or buccal administration, (such as self-propelling powder dispensing formulations described hereinafter), may comprise 0.1 to 20% w/w, for example 2% w/w of active ingredient.

The formulations, both for veterinary and for human medical use, of the present invention comprise an active ingredient in association with a pharmaceutically acceptable carrier therefor and optionally other therapeutic ingredient(s). The carrier(s) must be 'acceptable' in the sense of being compatible with the other ingredients of the formulations and not deleterious to the recipient thereof.

The formulations include those in a form suitable for oral, pulmonary, ophthalmic, rectal, parenteral (including subcutaneous, intramuscular, and intravenous), intraarticular, topical, nasal, or buccal administration.

The formulations may conveniently be presented in unit dosage form and may be prepared by any of the methods well-known in the art of pharmacy. All methods include the step of bringing the active ingredient into association with the carrier which constitutes one or more accessory ingredients. In general, the formulations are prepared by uniformly and intimately bringing the active ingredient into association with a liquid carrier or a finely divided solid carrier or both, and then, if necessary, shaping the product into the desired formulation.

Formulations of the present invention suitable for oral administration may be in the form of discrete units such as capsules, cachets, tablets, or lozenges, each containing a predetermined amount of the active ingredient; in the form of a powder or granules; in the form of a solution or a suspension in an aqueous liquid or nonaqueous liquid; or in the form of an oil-in-water emulsion or a water-in-oil emulsion. The active ingredient may also be in the form of a bolus, electuary, or paste.

A tablet may be made by compressing or molding the active ingredient optionally with one or more accessory ingredients. Compressed tablets may be prepared by compressing, in a suitable machine, the active ingredient in a free-flowing form such as a powder or granules, optionally mixed with a binder, lubricant, inert diluent, surface active, or dispersing agent. Molded tablets may be made by molding, in a suitable machine, a mixture of the powdered active ingredient and a suitable carrier moistened with an inert liquid diluent.

Formulations for rectal administration may be in the form of a suppository incorporating the active ingredient and a carrier such as cocoa butter, or in the form of an enema.

Formulations suitable for parenteral administration conveniently comprise a sterile aqueous preparation of the active ingredient which is preferably isotonic with the blood of the recipient.

Formulations suitable for intraarticular administration may be in the form of a sterile aqueous preparation of the active ingredient which may be in microcrystalline form, for example, in the form of an aqueous microcrystalline suspension. Liposomal formulations or biodegradable polymer systems may also be used to present the active ingredient for both intraarticular and ophthalmic administration.

Formulations suitable for topical administration include liquid or semi-liquid preparations such as liniments, lotions, applications, oil-in-water or water-in-oil emulsions such as creams, ointments or pastes; or solutions or suspensions such as drops. For example, for ophthalmic administration, the active ingredient may be presented in the form of aqueous eye drops as, for example, a 0.1–1.0% solution. Formulations suitable for administration to the nose or buccal cavity include powder, self-propelling and spray formulations such as aerosols and atomizers. The formulations, when dispersed, preferably have a particle size in the range of 0.1 to 200 $\mu$.

A particularly valuable form of a pharmaceutical composition of the present invention, for use in the prophylaxis or treatment of airway smooth muscle constriction, or asthma or bronchitis in general, due to any cause, is one suitable for pulmonary administration via the buccal cavity.

In addition to the aforementioned compound of the formula I, the formulations of this invention may include one or more additional active ingredients.

Any other therapeutic ingredient may comprise one or more of the following: antibiotic (e.g., anti-bacterial), antifungal and antiviral agents, and antihistamines (particularly peripherally acting antihistamines).

In addition to the compounds of formula I, the pharmaceutical compositions can also contain other active ingredients, such as cyclooxygenase inhibitors, nonsteroidal antiinflammatory drugs (NSAIDs), peripheral analgesic agents such as zomepirac, diflunisal, and the like. These other active ingredients are from those that are known in each of the named classes. The weight ratio of the compound of the formula I to the second active ingredient may be varied and will depend upon the effective dose of each ingredient. Generally, an effective dose of each will be used. Thus, for example, when a compound of the formula I is combined with an NSAID, the weight ratio of the compound of the formula I is combined with an NSAID, the weight ratio of the compound of formula I to the NSAID will generally range from about 1000:1 to about 1:1000, preferably about 200:1 to about 1:200. Combinations of a compound of the formula I and other active ingredients will generally also be within the aforementioned range, but in each case, an effective dose of each active ingredient should be used.

Combinations of a compound of the formula I and other active ingredients will generally be in the aforementioned ratios. However, when such other agent(s) are also present, according to another aspect of the invention, the compound of formula (I) or physiologically acceptable salt thereof and the other agent(s), need not necessarily be present as a pharmaceutical formulation as hereinbefore defined, but merely in combination or intimate admixture. Optionally, of course, a pharmaceutically acceptable carrier may be present.

The combination with antihistamines may be favored for antiasthmatic use. Such an antihistamine may be selected from any compound described in European Patent Applications EP 0 859 949 A and EP 0 117 302 A. The amount and dosage regime for such an antihistamine may be chosen from any of those recited in the latter two European Specifications. Especially preferred are the antihistamines (E)-3(6-(3-pyrrolidino)-1-(4-tolyl)prop-1E-enyl(-2-pyridyl)) acrylic acid and (E)-3-(6-(3-pyrrolidino)-1-(4-tolyl)prop-1E-enyl(-2-pyridyl))propionic acid. Another preferred antihistamine is (E)-1-(4-methylphenyl)-1-(2-pyridyl)-3-pyrrolidinoprop-1-ene, otherwise known as typrolidine.

Also preferred is the antihistamine known as Seldane.

The compound of formula I and their salts may be prepared generally by the following processes and constitute a further aspect of the present invention.

The compounds of the formula I are generally prepared by methods set out in the following Scheme I and Scheme II.

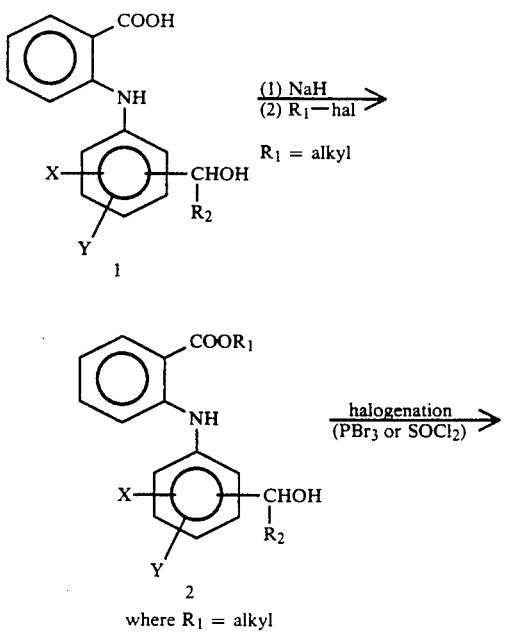

-continued
Scheme I

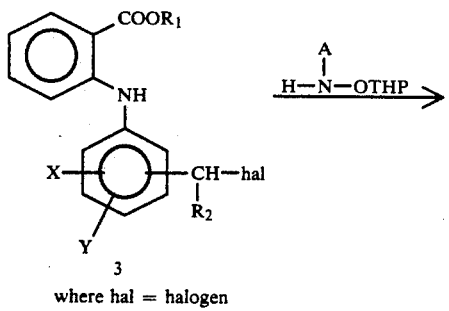

3
where hal = halogen
R₁ = alkyl

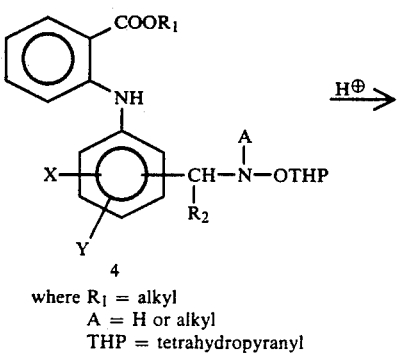

4
where R₁ = alkyl
A = H or alkyl
THP = tetrahydropyranyl

-continued
Scheme I

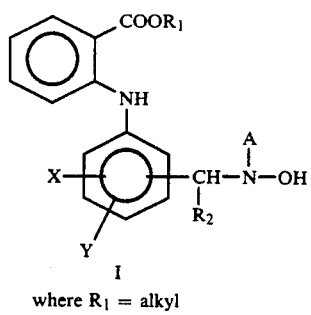

I
where R₁ = alkyl
A = H or alkyl

Starting carboxylic acids of the Formula 1 (Scheme I) are either known or may be prepared by standard methods and may be converted to the corresponding esters 2 by standard procedures. For example, see U.S. Pat. No. 3,413,313 or Kaltenbronn, et al, —Arzneimittel Forschung 33(1), 4a, 621 (1983). The hydroxylamines I (A=H, alkyl) may be prepared by alkylation of an O-protected hydroxylamine, followed by deprotection. That is, the alcohol of 2 may be converted to the halo derivative 3. Then the halo derivative can be reacted with 1 to 5 equivalents of an O-protected hydroxylamine such as O-tetrahydropyranylhydroxylamine in an organic solvent such as DMF at about 20° C. to 60° C. for 1 to 24 hours. Deprotection can be done under acidic conditions such as methanolic HCl at about 0° C. to reflux temperature for 15 minutes to 24 hours, or pyridinium p-toluene sulfonate in an alcohol solvent at about 0° C. to 60° C. for 15 minutes to 3 hours.

Scheme II

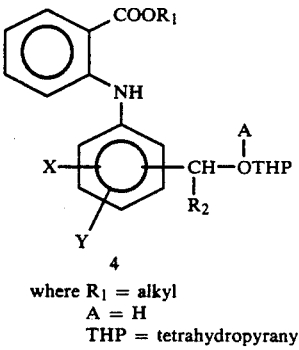

4
where R₁ = alkyl
A = H
THP = tetrahydropyranyl

| acid halide
or
acid anhydride
or
isocyanate
or
isothiocyanate
↓

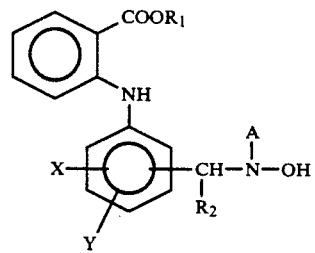

I
where R₁ = alkyl
A = H acid halide
or
acid anhydride
or
isocyanate
or
isothiocyanate
↙

XS
acid halide
or
acid anhydride
↘

-continued
Scheme II

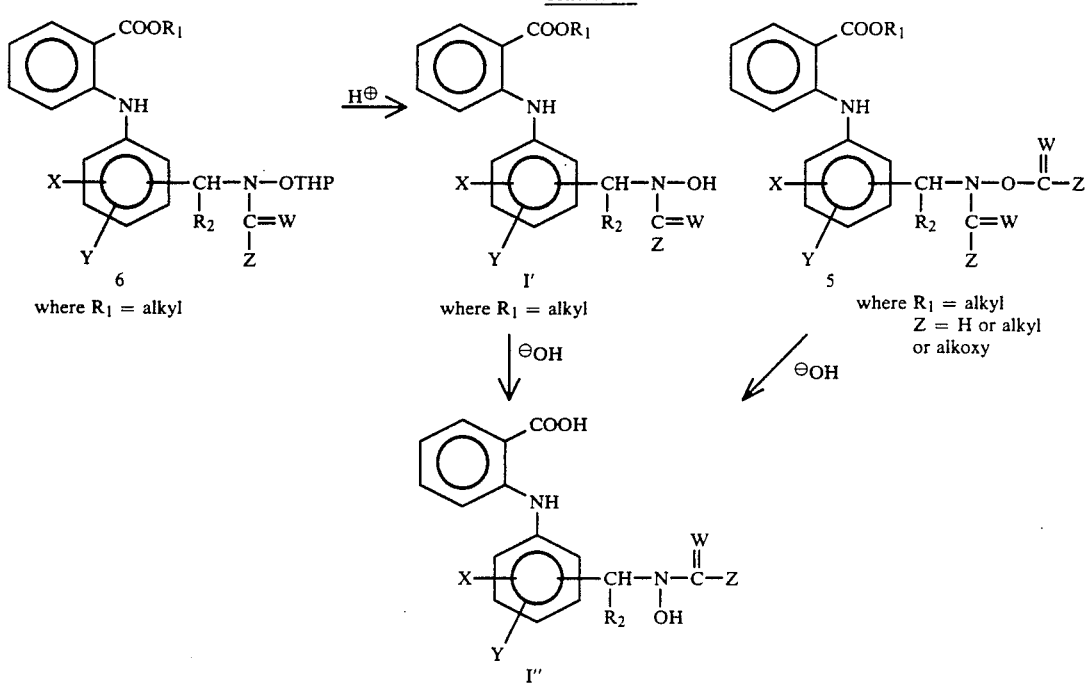

The hydroxylamines I (A=H) (Scheme II) are acylated with an acid chloride in dioxane/water in the presence of a base such as sodium acetate at about 5° C. to 30° C. for 30 minutes to 24 hours. Alternatively, they can be acylated with an excess of an acid chloride in a solvent such as methylene chloride in the presence of an organic base such as triethylamine or diisopropylamine at about 10° C. to 35° C. but preferably at room temperature. In the latter case, the diacylated product 5 is formed which is converted to I" by treatment with an aqueous inorganic base such as lithium hydroxide in an alcoholic solvent at about 20° C. to 40° C. preferably at room temperature.

The hydroxyureas I' ($R_1$=alkyl, W=O, Z=$NR_3R_4$) and hydroxythioureas I' ($R_1$=alkyl, W=S, Z=$NR_3R_4$) are prepared from the hydroxylamines I ($R_1$=alkyl, A=H) by reacting with the corresponding isocyanates or isothiocyanates in organic solvents such as toluene, or tetrahydrofuran, or toluene/tetrahydrofuran mixtures at about 10° C. to about 40° C. for 1 to 24 hours.

The intermediate O-protected hydroxylamines 4 alternatively may be reacted with the acid chloride or isocyanate or isothiocyanate according to the method described above for the O-unprotected hydroxylamines with the acid catalyzed deprotection following acylation.

The esters I' can be hydrolyzed to the carboxylic acids I" using an inorganic base such as potassium hydroxide in water or aqueous alcoholic solvents at 0° C. to room temperature for 1 to 12 hours.

The several reactions of this scheme show other means to prepare the compounds of the present invention using analogous methods well known in the art from starting materials that are known or can be readily prepared by known methods and variously exemplified hereinafter.

One of skill in the art would recognize variations in the sequence and would recognize variations in corresponding reaction conditions from analogous reactions which may be appropriately used in the processes to make the compounds of formula (1) herein. Further, the starting materials are known or can be prepared by known methods.

Under certain circumstances it is necessary to protect either the N or O of intermediates in the above noted process with suitable protecting groups which are known. Introduction and removal of such suitable oxygen and nitrogen protecting groups are well-known in the art of organic chemistry; see for example "Protective Groups in Organic Chemistry," J. F. W. McOmie, ed., (New York, 1973), pages 43ff, 95ff, J. F. W. McOmie, *Advances in Organic Chemistry*, Vol. 3, 191–281 (1963); R. A. Borssonas, *Advances in Organic Chemistry*, Vol. 3, 159–190 (1963); and J. F. W. McOmie, Chem. & Ind., 603 (1979).

Examples of suitable oxygen protecting groups are benzyl, t-butyldimethylsilyl, ethoxyethyl, and the like. Protection of an N-H containing moiety is necessary for some of the processes described herein for the preparation of compounds of this invention. Suitable nitrogen protecting groups are benzyl, triphenylmethyl, trialkylsilyl, trichloroethylcarbamate, trichloroethoxycarbonyl, vinyloxycarbamate, and the like.

Under certain circumstances it is necessary to protect two different oxygens with dissimilar protecting groups such that one can be selectively removed while leaving the other in place. The benzyl and t-butyldimethylsilyl groups are used in this way; either is removable in the presence of the other, benzyl being removed by catalytic hydrogenolysis, and t-butyldimethylsilyl being removed by reaction with, for example, tetra-n-butylammonium fluoride.

In the process described herein for the preparation of compounds of this invention the requirements for protective groups are generally well recognized by one skilled in the art of organic chemistry, and accordingly the use of appropriate protecting groups is necessarily implied by the processes of the charts herein, although not expressly illustrated.

The products of the reactions described herein are isolated by conventional means such as extraction, distillation, chromatography, and the like.

The salts of the compounds of formula (I) described above are prepared by reacting the appropriate base or acid with a stoichiometric equivalent of the compounds of formula (1), respectively, to obtain pharmaceutically acceptable salts thereof.

The invention is further elaborated by the representative examples as follows. Such examples are not meant to be limiting.

EXAMPLES

EXAMPLE 1

Ethyl 2-methyl-3-nitro-β-oxobenzenepropanoate

A solution of 2-methyl-3-nitrobenzoic acid (10.0 g, 55.2 mmol) and carbonyldiimidazole (13.4 g, 82.8 mmol) in tetrahydrofuran (200 mL) is stirred at room temperature for 2 hours under an argon atmosphere. The magnesium salt of malonic acid monoethyl ester (47.4 g, 165 mmol) is added and the reaction mixture is heated at reflux for 18 hours. The reaction mixture is quenched with water (200 mL) and acidified to pH=1 with concentrated HCl. The product is extracted into ethyl acetate and washed with 1.0 N HCl, saturated aqueous sodium bicarbonate, and brine. The organic layer is dried over magnesium sulfate and evaporated. Recrystallization of the residue gives ethyl 2-methyl-3-nitro-β-oxobenzenepropanoate (10.6 g, 76%), mp=50-51° C.

EXAMPLE 2

1-(2-Methyl-3-nitrophenyl)ethanone

A solution of ethyl 2-methyl-3-nitro-β-oxobenzenepropanoate (10.0 g, 39.7 mmol) in 100 mL of 30% water/trifluoroacetic acid is heated at reflux for 5 hours. The reaction mixture is cooled to room temperature, diluted with water (100 mL), and extracted with ether. The organic layer is washed with water, saturated aqueous sodium bicarbonate, and brine. Evaporation of the organic layer, followed by recrystallization of the residue gives 1-(2-methyl-3-nitrophenyl)ethanone (4.8 g, 67%), mp=49-51° C.

EXAMPLE 3

2,α-Dimethyl-3-nitrobenzenemethanol

Sodium borohydride (0.02 g, 0.6 mmol) is added to a solution of 1-(2-methyl-3-nitrophenyl)ethanone (0.2 g, 1.1 mmol) in methanol (50 mL) at 0° C. The reaction mixture is stirred at room temperature for 1.5 hours, and then is diluted with water (100 mL). The aqueous mixture is stirred at room temperature an additional 5 hours followed by extraction with ethyl acetate. The organic layer is washed with brine, dried over magnesium sulfate, and evaporated. Flash chromatography of the residue (silica, methylene chloride) gives 2,α-dimethyl-3-nitrobenzenemethanol (0.14 g, 77%) as an oil.

EXAMPLE 4

Ethyl 2-chloro-3-nitro-β-oxobenzenepropanoate

According to the procedure of Example 1, 2-chloro-3-nitrobenzoic acid (25 g, 121.6 mmol) is reacted with carbonyldiimidazole (23.7 g, 145.9 mmol) and the magnesium salt of malonic acid monoethyl ester (52.3 g, 182.4 mmol) to give ethyl 2-chloro-3-nitro-β-oxobenzenepropanoate (29.5 g, 89%), mp=49-52° C.

EXAMPLE 5

Ethyl 3-acetamido-2,4-dichloro-β-oxobenzenepropanoate

According to the procedure of Example 1, 3-acetamido-2,4-dichlorobenzoic acid (R. Leeper and A. Cooke, Pestic. Chem., Proc. 2nd Int. Congr. Pestic. Chem., Vol. 5, pp 125-139, 1972) (6.09 g, 24.5 mmol) is reacted with carbonyldiimidazole (4.77 g, 29.5 mmol) and the magnesium salt of malonic acid monoethyl ester (14 g, 49 mmol) to give ethyl 3-acetamido-2,4-dichloro-β-oxobenezenepropanoate (6.6 g, 85%), mp=103-105° C.

EXAMPLE 6

3-Amino-2,4-dichloro-α-methyl-benzenemethanol

A solution of ethyl 3-acetamido-2,4-dichloro-β-oxobenzene propanoate (6.6 g, 20.7 mmol) in trifluoroacetic acid (200 mL) and water (50 mL) is heated at reflux overnight. The solvent is evaporated and the residue taken up in ether. The resulting solution is washed with 10% aqueous sodium bicarbonate, dried over magnesium sulfate and evaporated. The crude ketone (3.0 g, 14.7 mmol) is dissolved in methanol (100 mL) and treated with sodium borohydride (0.28 g, 7.35 mmol) at 0° C. The reaction mixture is stirred at 0° C. for 1 hour and the solvent is evaporated. The residue is partitioned between ethyl acetate and water. The organic layer is dried over magnesium sulfate and evaporated. Flash chromatography (silica, 1:1 ether:hexane) provides pure 2-amino-2,4-dichloro-α-methyl-benzenemethanol (2.1 g, 69%) as an oil.

EXAMPLE 7

1-(2-Chloro-3-nitrophenyl)ethanone

According to the procedure of Example 2, ethyl 2-chloro-3-nitro-β-oxobenzenepropanoate (14.0 g, 51.5 mmol) is reacted with 30% water/trifluoroacetic acid to give 1-(2-chloro-3-nitrophenyl)ethanone (9.0 g, 87%), mp=41-43° C.

EXAMPLE 8

2-Chloro-α-methyl-3-nitrobenzenemethanol

According to the procedure of Example 3, 1-(2-chloro-3-nitrophenyl)ethanone (9.0 g, 44.6 mmol) is reacted with sodium borohydride (0.84 g, 22.3 mmol) to give 2-chloro-α-methyl-3-nitrobenzenemethanol (7.5 g, 83%), mp=62-64° C.

EXAMPLE 9

2-Chloro-3-nitrobenzenemethanol

A solution of 2-chloro-3-nitrobenzoic acid (1.0 g, 5.0 mmol) in tetrahydrofuran (10 mL) is cooled to 0° C. under an argon atmosphere. Boranetetrahydrofuran complex (6.4 mL of a 1.0 M solution) is added dropwise, maintaining a reaction temperature of less than 5° C. After the addition is complete, the reaction mixture is stirred for 6 hours at room temperature. It is then cooled in an ice bath and quenched by the addition of 10 mL of 1.0 N HCl. The reaction mixture is heated at reflux for 30 minutes and concentrated by distilling the THF. The remaining aqueous solution is extracted with methylene chloride, and the organic layer is washed with saturated aqueous bicarbonate and brine. Evaporation of the organic layer followed by recrystallization of the residue from hexane gives 2-chloro-3-nitrobenzenemethanol (0.4 g, 43%), mp=69–70° C.

EXAMPLE 10

3-Amino-2-methylbenzenemethanol

A solution of 2-methyl-3-nitrobenzenemethanol (10.0 g, 59.8 mmol) in methanol is treated with Raney Nickel and shaken under hydrogen gas (50 psi) in a Parr Shaker. The solution is filtered through Celite and evaporated. Recrystallization of the residue from isopropyl ether gives pure 3-amino-2-methylbenzenemethanol (7.4 g, 90%), mp=106–108° C.

The following compounds are prepared according to the procedure of Example 10.

TABLE 2

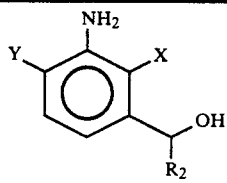

| Example | X  | Y | $R_2$ | Prepared from Compound of | % Yield | mp |
|---------|----|---|-------|---------------------------|---------|---------|
| 11      | Me | H | Me    | Ex. 3                     | 100%    | 85–87° C. |
| 12      | Cl | H | H     | Ex. 9                     | 38%     | 104–107° C. |
| 13      | Cl | H | Me    | Ex. 8                     | 82%     | 91–92° C. |

EXAMPLE 14

2-[[2-Chloro-3-(1-hydroxyethyl)phenyl]amino]benzoic acid

A mixture of diphenyliodonium-2-carboxylate monohydrate (11.4 g, 33.3 mmol), 3-amino-2-chloro-α-methylbenzenemethanol (5.2 g, 30.3 mmol), and cupric acetate (0.5 g) in isopropanol (100 mL) is heated at reflux for 12 hours under an argon atmosphere. The solvent is evaporated under vacuum and the remaining dark oil is taken up in 10% aqueous KOH. The insoluble material is removed by filtration through Celite-545, and the filtrate is extracted with ether to remove nonacidic impurities. The aqueous solution is acidified to pH=3 with concentrated HCl. The resulting precipitate is collected by filtration and purified by column chromatography (silica, ethyl acetate) to give pure 2-[[2-chloro-3-(1-hydroxyethyl)phenylamino]benzoic acid (5.8 g, 60%), mp=169–171° C.

The following compounds are prepared according to the procedure of Example 14.

TABLE 3

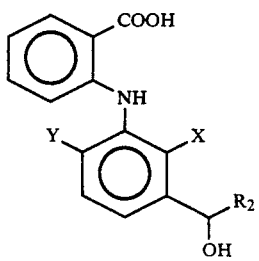

| Example | X  | Y  | $R_2$ | Prepared from Compound of | % Yield | mp |
|---------|----|----|-------|---------------------------|---------|---------|
| 15      | Me | H  | H     | Ex. 10                    | 71%     | 234–237° C. |
| 16      | Me | H  | Me    | Ex. 11                    | 72%     | 186–188° C. |
| 17      | Cl | H  | H     | Ex. 12                    | 83%     | 214–217° C. |
| 18      | Cl | Cl | Me    | Ex. 6                     | 78%     | dec 158–160° C. |

EXAMPLE 19

2-[[2-Chloro-3-(1-hydroxyethyl)phenyl]amino]benzoic acid methyl ester

Sodium hydride (0.48 g, 19.9 mmol) is added to a solution of 2-[[2-chloro-3-(1-hydroxyethyl)phenyl]amino]benzoic acid (5.8 g, 19.9 mmol) in dimethylformamide (15 mL) at room temperature. After 15 minutes, the reaction mixture is cooled to 0° C, and methyl iodide (2.8 g, 19.9 mmol) is added dropwise. The reaction mixture is stirred at room temperature overnight, and then partitioned between water and ether. The organic layer is washed with water and brine, dried over magnesium sulfate, and evaporated. Recrystallization of the residue from ether/hexane gives pure 2-[[2-chloro-3-(1-hydroxyethyl)phenyl]amino]benzoic acid methyl ester (4.6 g, 76%), mp=94–95° C.

The following compounds are prepared according to the procedure of Example 19.

TABLE 4

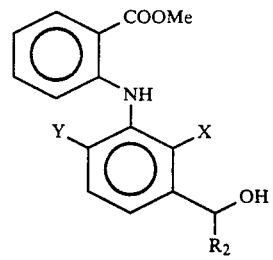

| Example | X  | Y  | $R_2$ | Prepared from Compound of | % Yield | mp |
|---------|----|----|-------|---------------------------|---------|---------|
| 20 | Me | H  | H  | Ex. 15 | 85% | 102–105° C. |
| 21 | Me | H  | Me | Ex. 16 | 78% | 102–103° C. |
| 22 | Me | Me | Me | Ref. U.S. Pat. No. 3,413,313 | 97% | 102–103° C. |
| 23 | Cl | H  | H  | Ex. 17 | 95% | 95–97° C. |
| 24 | Cl | Cl | H  | Meclomen Metabolite I | 92% | 137–139° C. |
| 25 | Cl | Cl | Me | Ex. 18 | 64% | |

EXAMPLE 26

2-[[3-[1-(N-hydroxyamino)ethyl]-2-methylphenyl]amino]benzoic acid methyl ester Phosphorus tribromide (4.2 mL, 1 M solution in dichloromethane) is added dropwise to a solution of 2-[[3-(1-hydroxyethyl)-2-methylphenyl]amino]benzoic acid methyl ester (2.0 g, 7.0 mmol) and pyridine (2 drops) in dicholoromethane (50 mL) at 0° C. After the reaction mixture is stirred at room temperature for 1 hour, it is poured into a solution of O-tetrahydropyranylhydroxylamine (8.2 g, 70 mmol) in dimethylformamide (50 mL). The dichloromethane is evaporated under reduced pressure, and the reaction mixture is stirred overnight at room temperature. The reaction mixture is diluted with 200 mL water and extracted with 300 mL ether. The organic layer is washed with water and brine, and then evaporated to an oil. The crude intermediate THP-protected hydroxylamine is taken up in methanol and acidified with concentrated HCl to pH=1. The reaction mixture is heated at reflux for 30 minutes, cooled, and quenched by the careful addition of saturated aqueous sodium bicarbonate. The methanol is evaporated under reduced pressure and the product is extracted into ethyl acetate. The organic layer is washed with brine, dried over magnesium sulfate, and evaporated to give the crude hydroxylamine as an oil.

The residue is taken up in ether/hexane and filtered through a pad of silica gel, which is first eluted with 50% ether/hexane and then with ether. The ether eluant is evaporated to give 2-[[3-[1-(N-hydroxyamino)ethyl]-2-methylphenyl]amino]benzoic acid methyl ester (0.95 g, 45%), mp=114-116° C.

The following compounds are prepared according to the procedure of Example 26.

TABLE 5

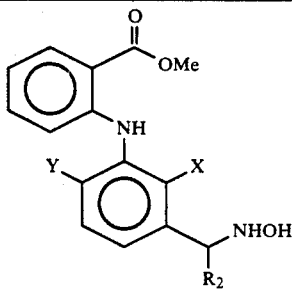

| Example | X | Y | $R_2$ | Prepared from Compound of | % Yield | mp |
|---|---|---|---|---|---|---|
| 27 | Me | H | H | Ex. 20 | 27% | 107-109° C. |
| 28 | Me | Me | Me | Ex. 22 | 27% | 112-114° C. |
| 29 | Cl | H | H | Ex. 23 | 83% | 103-105° C. |
| 30 | Cl | H | Me | Ex. 19 | 81% | 90-92° C. |
| 31 | Cl | Cl | H | Ex. 24 | 53% | 158-161° C. |
| 32 | Cl | Cl | Me | Ex. 25 | 60% | 124-130° C. |

EXAMPLE 33

3-[[1-(Acetylhydroxyamino)ethyl]-2-chlorophenyl]amino]benzoic acid methyl ester

Acetyl chloride (0.49 g, 6.2 mmol) is added dropwise to a mixture of 2[[2-chloro-3-[1-(N-hydroxyamino)ethyl]phenyl]amino]benzoic acid methyl ester (2.0 g, 6.2 mmol) and sodium acetate (0.77 g, 9.4 mmol) in 2:1 dioxane:water with ice bath cooling. The reaction mixture is stirred at room temperature overnight. It is then diluted with water (100 mL) and extracted with ethyl acetate (200 mL). The organic layer is washed with water (200 mL) and brine (100 mL), and is dried over magnesium sulfate. Evaporation of the ethyl acetate gives the crude product which is purified by flash chromatography (silica, 50% ethyl acetate/hexane). Recrystallization gives 2-[[3-[1-(acetylhydroxyamino)ethyl]-2-chlorophenyl]amino]benzoic acid methyl ester (0.34 g, 15%). mp=171-172° C.

The following compounds are prepared according to the procedure of Example 33.

TABLE 6

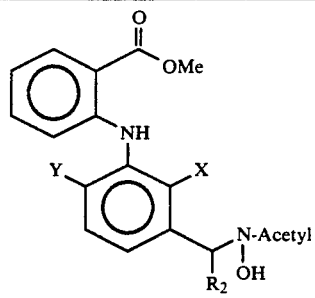

| Example | X | Y | $R_2$ | Prepared from Compound of | % Yield | mp |
|---|---|---|---|---|---|---|
| 34 | Me | H | H | Ex. 27 | 31% | 95-97° C. |
| 35 | Me | H | Me | Ex. 26 | 54% | 191-192° C. |
| 36 | Me | Me | Me | Ex. 28 | 74% | 183-184° C. |
| 37 | Cl | H | H | Ex. 29 | 18% | 200° C. dec |
| 38 | Cl | Cl | H | Ex. 31 | 36% | 172-173° C. |
| 39 | Cl | Cl | Me | Ex. 32 | 40% | 183-185° C. |

EXAMPLE 40

2[[Chloro-3-[[ethoxycarbonyl)hydroxyamino]methyl]phenylamino]benzoic acid methyl ester Thionyl chloride (1.2 g, 10.3 mmol) is added dropwise to a solution of 2-[[2-chloro-3-(hydroxymethyl)phenyl]amino]benzoic acid methyl ester (1.5 g, 5.14 mmol) and pyridine (0.08 g, 10.3 mmol) in ether (100 mL) at 0° C. under argon. The reaction mixture is stirred at room temperature for 30 minutes and then quenched by the addition of 100 mL of 1N HCl. The layers are separated and the organic layer is washed with 200 mL of saturated aqueous sodium bicarbonate, dried over magnesium sulfate, and evaporated to give the crude chloro derivative which is not purified but used directly in the next reaction.

N-ethoxycarbonyl-0-tetrahydropyranyl hydroxylamine (1.8 g, 10.3 mmol) is added to a slurry of sodium hydride (0.25 g, 10.3 mmol) in dimethylformamide at 0° C. The reaction mixture is allowed to warm to room temperature. A solution of the crude chloro derivative from above, in dimethylformamide (20 mL) is added, followed by the addition of sodium iodide (0.77 g, 5.14 mmol). The reaction mixture is heated at 65° C. for 1 hour. It is cooled, treated with 200 mL of saturated aqueous ammonium chloride, and extracted with ethyl acetate (400 mL). The organic layer is washed with water (400 mL) and brine (200 mL). The solvent is evaporated under vacuum and the residue is taken up in 100 mL methanol. Concentrated HCl (3 mL) is added and the reaction mixture is stirred at room temperature for 2 hours. The reaction is quenched by the dropwise addition of saturated aqueous sodium bicarbonate and the product is extracted into ethyl acetate. The organic layer is washed with brine and dried over magnesium sulfate. Evaporation of the solvent, followed by flash chromatography (silica, 40% ethyl acetate/hexane) gives pure 2-[[2-chloro-3[[(ethoxycarbonyl)hydroxyamino]methyl]phenyl]amino]benzoic acid methyl ester (0.14 g, 7%). mp=108-110° C.

EXAMPLE 41

2-[[3-[[(Ethoxycarbonyl)hydroxyamino]methyl]-2-methylphenyl]amino]benzoic acid methyl ester Ethyl chloroformate (0.57 g, 5.2 mmol) is added dropwise to a mixture of 2-[3-(N-hydroxyamino)methyl-2-methylphenyl]amino]benzoic acid methyl ester (1.5 g, 5.2 mmol) and sodium acetate (0.64 g, 7.8 mmol) in 33% water/dioxane with ice bath cooling. The reaction mixture is stirred at room temperature for 30 minutes. It is then diluted with water (100 mL) and extracted with ethyl acetate (200 mL). The organic layer is washed with water (200 mL) and brine (100 mL), and is dried over magnesium sulfate. Evaporation of the ethyl acetate gives the crude product which is purified by flash chromatography (silica, 50% ether/hexane). Recrystallization from ether gives 2-[[3-[[(ethoxycarbonyl)hydroxyamino]methyl]-2-methylphenyl]amino]benzoic acid methyl ester (1.1 g, 59%). mp=101-103° C.

The following compounds are prepared according to the procedure of the specified examples.

TABLE 7

| Example | X,Y,R$_2$ | Prepared from Compound of | According to Procedure of | % Yield | mp |
|---|---|---|---|---|---|
| 42 | Cl,Cl,H | Ex. 31 | Ex. 41 | 40% | 81-84° C. |
| 43 | Me,Me,Me | Ex. 22 | Ex. 40 | 15% | 57-60° C. |

EXAMPLE 44

2-[[3-[[Hydroxy[(methylamino)carbonyl]amino]methyl]-2-methylphenyl]amino]benzoic acid methyl ester Methyl isocyanate (0.33 g, 5.8 mmol) is added dropwise to 2-[[3-(N-hydroxyamino)methyl-2-methylphenyl]amino]benzoic acid methyl ester (1.5 g, 5.2 mmol) in 33% water/dioxane (60 mL) with ice bath cooling. The reaction mixture is stirred at 0° C. for 30 minutes and then at room temperature for 1 hour. It is then diluted with water (100 mL) and extracted with ethyl acetate (200 mL). The organic layer is washed with water (50 mL) and dried over magnesium sulfate. Evaporation of the ethyl acetate gives the crude product which is purified by recrystallization first from ether and then from ethyl acetate to give 2-[[3-[[hydroxy[(methylamino)carbonyl]amino]methyl]2-methylphenyl]amino]benzoic acid methyl ester (0.68 g, 38%). mp=173-175° C.

EXAMPLE 45

2-[[2-Chloro-3-[[0-tetrahydropyranyl)hydroxyamino]methyl]phenyl]amino]benzoic acid methyl ester Phosphorus tribromide (8.4 mL, in 1 M solution in dichloromethane) is added dropwise to a solution of 2-[[2-chloro-3-(hydroxymethyl)phenyl]amino]benzoic acid methyl ester (4.1 g, 14.0 mmol) and pyridine (2 drops) in dichloromethane (50 mL) at 0° C. The reaction mixture is stirred at 0° C. for 10 minutes and at room temperature for 90 minutes. When the reaction is complete, it is extracted with brine (5×100 mL) until subsequent washings are neutral. Evaporation of the organic layer gives the crude benzyl bromide which is then added to a mixture of 0-tetrahydropyranylhydroxylamine (3.4 g, 28.1 mmol) and sodium bicarbonate (5.9 g, 70.3 mmol) in dimethylformamide. The reaction mixture is stirred at room temperature for 12 hours, and then partitioned between water (200 mL) and ether (200 mL). The organic layer is washed with water (200 mL) and brine (100 mL), dried over magnesium sulfate, and concentrated under vacuum. The residue is taken up in methylene chloride and filtered through a pad of silica gel, which is eluted first with methylene chloride and then with ether. Evaporation of the ether eluant gives 2-[[2-chloro-3-[[0-(tetrahydropyranyl)hydroxyamino]methyl]phenyl]amino]benzoic acid methyl ester (3.4 g, 62%) as an oil.

EXAMPLE 46

2-[[2-Chloro-3-[[hydroxy[(methylamino)carbonyl]amino]methyl]phenyl]amino]benzoic acid methyl ester Methyl isocyanate (0.19 g, 3.4 mmol) is added dropwise to 2-[[2-chloro-3-[[0-(tetrahydropyranyl)hydroxyamino]methyl]phenyl]aminobenzoic acid methyl ester (1.2 g, 3.1 mmol) in 33% water/dioxane (20 mL) with ice bath cooling. The reaction mixture is stirred at room temperature overnight. It is then diluted with water (100 mL) and extracted with ethyl acetate (300 mL). The organic layer is washed with brine (300 mL) and evaporated. The remaining oil is taken up in 50 mL of 10% water in methanol and acidified to pH=1 with concentrated HCl. The reaction mixture is stirred at room temperature for 2 hours. The reaction is quenched by the dropwise addition of saturated aqueous sodium bicarbonate and then stirred for 10 minutes at room temperature. The resulting precipitate is collected by filtration and recrystallized from ethyl acetate/hexane to give pure 2-[[2-chloro-3-[[hydroxy[(methylamino)carbonyl]amino]methyl]phenyl]amino]benzoic acid methyl ester (0.51 g, 45%). mp=143-145° C.

EXAMPLE 47

2-[[3-[1-Acetylhydroxyamino)ethyl]-2-chlorophenyl]amino]benzoic acid

2-[[3-[1-(Acetylhydroxyamino)ethyl]-2-chlorophenyl]amino]benzoic acid methyl ester (0.24 g, 0.7 mmol) is suspended in 150 mL of 1 N potassium hydroxide containing 10 mL methanol. The reaction mixture is stirred until all the solid is dissolved (about 2 hours). It is acidified to pH=1 with concentrated HCl and the resulting precipitate is collected by filtration. Recrystallization from ethyl acetate gives 2-[[3-[1-[acetylhydroxyamino)ethyl]-2-chlorophenyl]amino]benzoic acid (74 mg, 32 %) as a hydrate. mp=162-164° C. dec.

The following compounds are prepared according to the procedure of Example 47.

TABLE 8

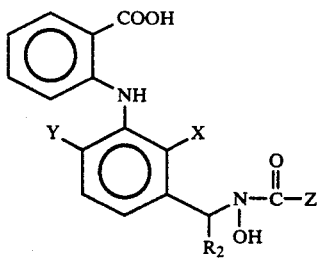

| Example | X,Y | $R_2$ | Z | Prepared from Compound of | % Yield | mp |
|---|---|---|---|---|---|---|
| 48 | Me,H | H | Me | Ex. 34 | 23% | 147–150° C. dec |
| 49 | Me,H | H | OEt | Ex. 41 | 87% | 203–204° C. dec |
| 50 | Me,H | H | NHMe | Ex. 44 | 75% | 165–167° C. dec |
| 51 | Me,H | Me | Me | Ex. 35 | 39% | 212–214° C. dec |
| 52 | Me,Me | Me | Me | Ex. 36 | 80% | 125° C. dec |
| 53 | Me,Me | Me | OEt | Ex. 43 | 75% | 105° C. dec |
| 54 | Cl,H | H | Me | Ex. 37 | 66% | 181–182° C. dec |
| 55 | Cl,Cl | H | Me | Ex. 38 | 45% | 201–206° C. |
| 56 | Cl,Cl | H | OEt | Ex. 42 | 74% | 180–184° C. |
| 57 | Cl,Cl | Me | Me | Ex. 39 | 52% | 196–197° C. dec |

We claim:

1. A compound of the formula (I)

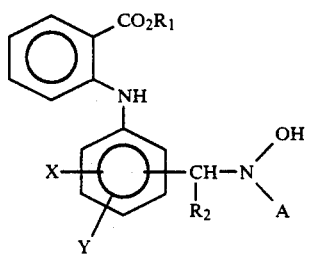

or a pharmaceutically acceptable base; acid or base salt thereof; or acid addition salt thereof; wherein $R_1$ is hydrogen or lower alkyl;
$R_2$ is hydrogen or lower alkyl;
X is hydrogen, halogen, trifluoromethyl, lower alkyl, lower alkoxy, or hydroxy;
Y is hydrogen, halogen, trifluoromethyl, lower alkyl, lower alkoxy, or hydroxy;
A is H, lower alkyl, or

wherein W is S or O and Z is H, lower alkyl, lower alkoxy or $NR_3R_4$ wherein $R_3$ and $R_4$ are independently hydrogen or lower alkyl.

2. A compound of claim 1 wherein A is

having W and Z as defined above and $R_1$, $R_2$, X, and Y are as defined above.

3. A compound of claim 1 wherein A is H or lower alkyl and $R_1$, $R_2$, X, and Y are as defined above.

4. A compound of claim 2 wherein $R_1$ is hydrogen.

5. A compound of claim 2 wherein $R_2$ is lower alkyl.

6. A compound of claim 3 wherein $R_1$ is hydrogen.

7. A compound of claim 3 wherein $R_2$ is lower alkyl.

8. A compound of claim 1 which is 2-[[3-[1-(acetylhydroxyamino)ethyl]-2,6-dimethylphenyl]amino]benzoic acid methyl ester.

9. A compound of claim 1 which is 2-[[3-[1-[(ethoxycarbonyl)hydroxyamino]ethyl]-2,6-dimethylphenyl]amino]benzoic acid methyl ester.

10. A compound of claim 1 which is 2-[[3-[1-(acetylhydroxyamino)ethyl]-2,6-dimethylphenyl]amino]benzoic acid.

11. A compound of claim 1 which is 2-[[3-[1-[ethoxycarbonyl)hydroxyamino]ethyl]-2,6-dimethylphenyl]amino]benzoic acid.

12. A compound of claim 1 which is 2-[[3-[(acetylhydroxyamino)methyl]2-chlorophenyl]amino]benzoic acid methyl ester.

13. A compound of claim 1 which is 2-[[2-chloro-3[[(ethoxycarbonyl)hydroxyamino]methyl]phenyl]amino]benzoic acid methyl ester.

14. A compound of claim 1 which is 2-[[2-chloro-3[[hydroxy[(methylamino)carbonyl]amino]methyl]phenyl]amino]benzoic acid methyl ester.

15. A compound of claim 1 which is 2-[[3-[1-(acetylhydroxyamino)ethyl]-2-chlorophenyl]amino]benzoic acid methyl ester.

16. A compound of claim 1 which is 2-[[3-[(acetylhydroxyamino)methyl]-2-chlorophenyl]amino]benzoic acid.

17. A compound of claim 1 which is 2-[[3-[1-(acetylhydroxyamino)ethyl]-2-chlorophenyl]amino]benzoic acid.

18. A compound of claim 1 which is 2-[[3-[(acetylhydroxyamino)methyl]-2-methylphenyl]amino]benzoic acid.

19. A compound of claim 1 which is 2-[[3-[(acetylhydroxyamino)methyl]-2-methylphenyl]amino]benzoic acid methyl ester 20. A compound of claim 1 which is 2-[[3-[[hydroxy[(methylamino)carbonyl]amino]methyl]-2-methylphenyl]amino]benzoic acid methyl ester.

21. A compound of claim 1 which is 2-[[3-[[ethoxycarbonyl)hydroxyamino]methyl]-2-methylphenyl]amino]benzoic acid methyl ester.

22. A compound of claim 1 which is 2-[[3-[1-(acetylhydroxyamino)ethyl]-2-methylphenyl]amino]benzoic acid methyl ester.

23. A compound of claim 1 which is 2-[[3-[[hydroxy[(methylamino)carbonyl]amino]methyl]-2-methylphenyl]amino]benzoic acid.

24. A compound of claim 1 which is 2-[[3-[[(ethoxycarbonyl)hydroxyamino]methyl]-2-methylphenyl]amino]benzoic acid.

25. A compound of claim 1 which is 2-[[3-[(acetylhydroxyamino)methyl]2,6-dichlorophenyl]amino]benzoic acid methyl ester.

26. A compound of claim 1 which is 2-[[2,6-dichloro3-[[(ethoxycarbonyl)hydroxyamino]methyl]phenyl]amino]benzoic acid methyl ester.

27. A compound of claim 1 which is 2-[[3-2-(acetylhydroxyamino)ethyl-2-methylphenyl]amino]benzoic acid.

28. A compound of claim 1 which is 2-[[2,6-dichloro3[[(ethoxycarbonyl)hydroxyamino]methyl]phenyl]amino]benzoic acid.

29. A compound of claim 1 which is 2-[[3-[(acetylhydroxyamino)methyl]-2,6-dichlorophenyl]amino]benzoic acid.

30. A compound of claim 1 which is 2-[[3-[1-(acetyl-hydroxyamino)ethyl]-2,6-dichlorophenyl]amino]benzoic acid.

31. A compound of claim 1 which is 2-[[3-[1-(acetyl-hydroxyamino)ethyl]-2,6-dichlorophenyl]amino]benzoic acid methyl ester.

32. A compound of claim 3 which is 2-[[3-[1-(Nhydroxyamino)ethyl]-2-methylphenyl]amino]benzoic acid methyl ester.

33. A compound of claim 3 which is 2[[3-[(hydroxyamino)methyl]-2-methylphenyl]amino]benzoic acid methyl ester.

34. A compound of claim 3 which is 2-[[2,6-dimethyl3-[1-hydroxyamino)ethyl]phenyl]amino]benzoic acid methyl ester.

35. A compound of claim 3 which is 2-[2-chloro-3[(hydroxyamino)methyl]phenyl]amino]benzoic acid methyl ester.

36. A compound of claim 3 which is 2-[[2-chloro-3-[1hydroxyamino)ethyl]phenyl]amino]benzoic acid methyl ester.

37. A compound of claim 3 which is 2-[2,6-dichloro3-[(hydroxyamino)methyl]phenyl]amino]benzoic acid methyl ester.

38. A compound of claim 3 which is 2-[2,6-dichloro3-[1-(hydroxyamino)ethyl]phenyl]amino]benzoic acid methyl ester.

39. A pharmaceutical composition for treating inflammation which comprises an antiinflammatory effective amount of a compound of claim 1 and a pharmaceutically acceptable carrier.

40. A method for treating inflammation in a human suffering from inflammation which comprises administering a compound of claim 1 in unit dosage form.

* * * * *

UNITED STATES PATENT AND TRADEMARK OFFICE
CERTIFICATE OF CORRECTION

PATENT NO. : 5,017,604    Page 1 of 2
DATED : MAY 21, 1991
INVENTOR(S) : BELLIOTTI ET AL.

It is certified that error appears in the above—identified patent and that said Letters Patent is hereby corrected as shown below:

Column 22, line 19:
   change "3[[(ethoxycarbonyl)hydroxyamino]methyl]phenyl-" to
      -- 3-[[(ethoxycarbonyl)hydroxyamino]methyl]phenyl- --.

Column 22, line 63:
   change "28. A compound of claim 1 which is 2-[[2,6-dichloro3
   to -- 28. A compound of claim 1 which is 2-[[2,6-dichloro-3-

Column 23, line 19:
   change "thyl3-[1-hydroxyamino)ethyl]phenyl]amino]benzoic" to
      -- thyl-3-[1-(hydroxyamino)ethyl]phenyl]amino]benzoic --.

Column 24, line 7:
   change "37. A compound of claim 3 which is 2-[2,6-dichloro3-
   to -- 37. A compound of claim 3 which is 2-[[2,6-dichloro-3-

Column 24, line 10:
   change "38. A compound of claim 3 which is 2-[2,6-dichloro3-
   to -- 38. A compound of claim 3 which is 2-[[2,6-dichloro-3-

UNITED STATES PATENT AND TRADEMARK OFFICE
CERTIFICATE OF CORRECTION

PATENT NO. : 5,017,604

DATED : MAY 21, 1991

INVENTOR(S) : BELLIOTTI ET AL.

It is certified that error appears in the above—identified patent and that said Letters Patent is hereby corrected as shown below:

Column 22, line 60:

change "27. A compound of claim 1 which is 2-[[3-2-(acetyl-" to -- 27. A compound of claim 1 which is 2-[[3-[2-(acetyl --

Column 22, line 61:

change "hydroxyamino)ethyl-2-methylphenyl]amino]" to -- h droxyamino)ethyl]-2-methylphenyl]amino] --.

Column 23, line 9:

change "32. A compound of claim 3 which is 2-[[3-[1-(Nhy-" to -- 32. A compound of claim 3 which is 2-[[3-[1-(N-hy --.

Signed and Sealed this

Twenty-ninth Day of December, 1992

*Attest:*

DOUGLAS B. COMER

*Attesting Officer*   *Acting Commissioner of Patents and Trademarks*